United States Patent
Zhang et al.

(10) Patent No.: US 9,018,213 B2
(45) Date of Patent: Apr. 28, 2015

(54) ALICYCLIC[C] BENZOPYRONE DERIVATIVES AND USES THEREOF

(75) Inventors: Guisen Zhang, Xuzhou (CN); Yin Chen, Jiangsu (CN); Xiangqing Xu, Jiangsu (CN); Xin Liu, Hubei (CN); Song Zhao, Jiangsu (CN); Bifeng Liu, Hubei (CN); Minquan Yu, Jiangsu (CN); Yinli Qiu, Jiangsu (CN)

(73) Assignees: Huazhong University of Science & Technology, Hubei (CN); NHWA Pharma. Corporation, Jiangsu (CN)

( * ) Notice: Subject to any disclaimer, the term of this patent is extended or adjusted under 35 U.S.C. 154(b) by 0 days.

(21) Appl. No.: 14/236,208

(22) PCT Filed: Jul. 31, 2012

(86) PCT No.: PCT/CN2012/079413
§ 371 (c)(1),
(2), (4) Date: Jan. 30, 2014

(87) PCT Pub. No.: WO2013/017071
PCT Pub. Date: Feb. 7, 2013

(65) Prior Publication Data
US 2014/0171442 A1 Jun. 19, 2014

(30) Foreign Application Priority Data
Aug. 3, 2011 (CN) .......................... 2011 1 0220962

(51) Int. Cl.
*A61K 31/496* (2006.01)
*A61K 31/453* (2006.01)
*A61K 31/454* (2006.01)
*C07D 311/94* (2006.01)
*C07D 405/12* (2006.01)
*C07D 417/12* (2006.01)
*C07D 417/14* (2006.01)
*C07D 413/14* (2006.01)
*C07D 311/80* (2006.01)
*C07D 409/12* (2006.01)

(52) U.S. Cl.
CPC ............ *C07D 311/94* (2013.01); *C07D 417/14* (2013.01); *A61K 31/496* (2013.01); *A61K 31/454* (2013.01); *A61K 31/453* (2013.01); *C07D 413/14* (2013.01); *C07D 311/80* (2013.01); *C07D 405/12* (2013.01); *C07D 417/12* (2013.01); *C07D 409/12* (2013.01)

(58) Field of Classification Search
None
See application file for complete search history.

(56) References Cited

U.S. PATENT DOCUMENTS

| 4,025,630 A | 5/1977 | Dren et al. |
| 4,382,943 A | 5/1983 | Winter et al. |
| 4,569,994 A | 2/1986 | Griffith |
| 5,359,098 A | 10/1994 | Erickson et al. |
| 5,428,038 A | 6/1995 | Chatterjee et al. |

FOREIGN PATENT DOCUMENTS

| CN | 201110086701.8 | 4/2011 |
| CN | 102267971 | 12/2011 |

OTHER PUBLICATIONS

Yagcioglu, Turkish Journal of Psychiatry, vol. 18(4), p. 1-10 (2007).*
International Search Report for Application. No. PCT/CN2012/079413 dated Nov. 15, 2012.
Martin Winn et al., Drugs Derived from Cannabinoids. 5. $\Delta^{6a,10a}$ Tetrahydrocannabinol and Heterocyclic Analogs Containing Aromatic Side Chains; Journal of Medicinal Chemistry Laboratories, 1976, vol. 19, No. 4, pp. 461-471.

* cited by examiner

*Primary Examiner* — Emily Bernhardt
(74) *Attorney, Agent, or Firm* — Frommer Lawrence & Haug LLP

(57) ABSTRACT

Disclosed are alicyclic[c]benzopyrone derivatives and use thereof. The alicyclic[c]benzopyrone derivatives are compounds represented by formula I or their salts. The present compounds not only significantly improve high activity induced by MK-801, but also effectively improve clambering symptom induced by Apomorphine and do not cause EPS within effective dose. These in vitro targets and in vivo pharmacological models are closely related to diseases of the nervous system caused by dopamine dysfunction, especially schizophrenia. Therefore the present compounds can be used for the treatment of central nervous system diseases, especially schizophrenia. $ED_{50}$ is lower and effect is stronger in two animal models i.e. high activity induced by MK-801 and clambering symptom induced by Apomorphine, while $ED_{50}$ is higher and therapeutic index is greater in animal models of catalepsy.

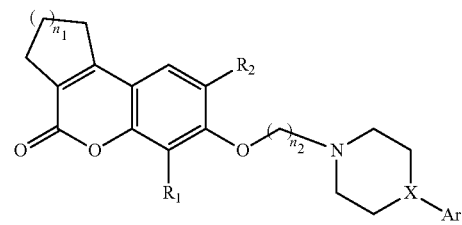

17 Claims, No Drawings

ALICYCLIC[C] BENZOPYRONE DERIVATIVES AND USES THEREOF

The present application claims priority from PCT/CN2012/079413 filed on Jul. 31, 2012, which claims priority from Chinese Patent Application No. CN 201110220962.4 filed on Aug. 3, 2011, the disclosures of which are incorporated herein by reference in their entirety.

FIELD OF THE INVENTION

The invention relates to the medicinal chemistry field. In particular, the invention relates to an alicyclic[c]benzopyrone derivative and the use thereof for the treatment or prevention of central nervous system diseases.

It is noted that citation or identification of any document in this application is not an admission that such document is available as prior art to the present invention.

The anti-psychosis drug exerting its pharmacological action by blocking dopamine $D_2$ receptor is conventionally known as the $1^{st}$ generation anti-psychosis drug, i.e. the "typical" anti-psychosis drug (e.g. haloperidol). This drug is effective for schizophrenia positive symptoms, but not effective for negative symptoms and cognitive disorders. Furthermore, the typical anti-psychosis drug generally has serious extrapyramidal system (EPS) side effects and is not effective for ⅓ of the patients with schizophrenia.

A series of new anti-psychosis drugs have been developed since 1960s, including ziprasidone, risperidone or the like, which are considered as the $2^{nd}$ generation anti-psychosis drug (the novel anti-psychosis drug). Although these drugs have different pharmacological actions, they share the same pharmacological properties, i.e. the affinities for 5-hydroxy tryptamine (5-HT) receptors (5-$HT_{1A}$, 5-$HT_{2A}$, 5-$HT_{2C}$) and noradrenalin (NA) receptors (α1, α2) are much higher than those for $D_2$ receptor, resulting the decrease of the ratio $D_2$/5-$HT_{2A}$. Their clinical effects are more advantageous over those of the $1^{st}$ generation anti-psychosis drugs, since they are effective for the positive symptoms like the conventional anti-psychosis drug, and are effective for the negative symptoms and cognitive defect symptoms, and have broader application spectrum. However, these drugs have the side effects of extended QT interval, hyperprolactinemia, weight gain or the like. Therefore, it is needed to find a new drug, which is effective for schizophrenia positive and negative symptoms and cognitive disorders, and has fewer side effect.

5-hydroxy tryptamine system plays an important role in modulating the function of prefrontal cortex (PFC), including emotion control, cognitive behavior and working memory. The pyramidal neurons and GABA interneurons of PFC contain several hydroxy tryptamine receptor subtypes 5-$HT_{1A}$ and 5-$HT_{2A}$ in high density. It has been shown recently that PFC and NMDA receptor channels are the targets of 5-$HT_{1A}$ receptor, and these two receptors modulate the excitatory neuron of cerebral cortex, thereby affecting the cognitive function. In fact, various preclinical data have shown that 5-$HT_{1A}$ receptor may be the new target of the development of anti-psychosis drug. The high affinity of a non-typical anti-psychosis drug (e.g. olanzapine, aripiprazole or the like) to 5-$HT_{1A}$ receptor and its low EPS side effects indicate that 5-hydroxy tryptamine system plays an important role in modulating the function of prefrontal cortex (PFC), including emotion control, cognitive behavior and working memory. The pyramidal neurons and GABA interneurons of PFC contain several 5-hydroxy tryptamine receptor subtypes 5-$HT_{1A}$ and 5-$HT_{2A}$ in high density. It has been shown recently that 5-$HT_{1A}$ agonist is associated with non-typical anti-psychosis drug therapy, which can improve negative symptoms and cognitive disorders. In the treatment of schizophrenia with the non-typical anti-psychosis drug clozapine, it was found that 5-$HT_{2A}$ plays an important role in various aspects, including cognition, emotion regulation and motion control. The blocking of 5-$HT_{2A}$ receptor can normalize the release of dopamine, exerting the effect of anti-psychosis. In addition, 5-$HT_{2C}$ receptor is closely related with weight gain.

The distribution of $D_3$ receptor in brain mainly locates specifically at the limbic system and there are two major DA neural pathways in brain: one is nigrostriatal pathway regulating the motion function, and the other is mesencephalic ventral tegmental area-accumbens nucleus-prefrontal cortex. DA pathway is closely associated with learning cognition and emotion behavior, of which the disorder will lead to schizophrenia. This DA pathway is the main pathway of reward effect in brain. $D_3$ receptor is distributed in both of the DA neural pathways, and has complex interaction with other DA receptor subtypes, and thus may be the target of anti-psychosis drug therapy. Selective $D_3$ receptor antagonism can reduce the negative and cognitive symptoms of schizophrenia, which can additionally prevent extrapyramidal system side effects, including tardive dyskinesia, Parkinson's disease or the like. Therefore, it is needed to find novel anti-schizophrenia drug which can bind to multiple receptors and has less side effects clinically.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is an object of the invention to provide a novel alicyclic [c]benzopyrone derivative with greater pharmaceutical activity so as to meet clinical requirements.

The compound according to the invention is the alicyclic [c]benzopyrone derivative with the following formula or a salt thereof:

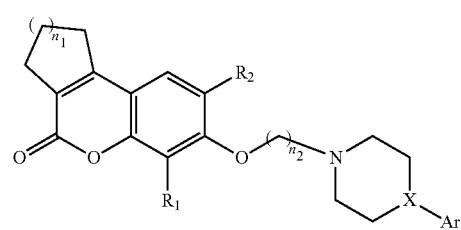

wherein
n₁ is 1, 2 or 3;
n₂ is 3, 4 or 5;
X is CH or N;
Ar has the formula II or formula III

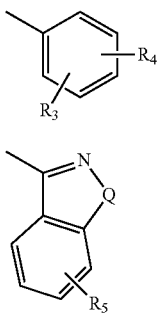

wherein
Q is O or S;
$R_1$, $R_2$, $R_3$, $R_4$ or $R_5$ each independently represents H, halogen, unsubstituted C1-C5alkyl, C1-C5alkyl substituted by halogen, unsubstituted C1-C5alkoxy or C1-C5alkoxy substituted by halogen, wherein the C1-C5alkyl and C1-C5alkoxy are preferably substituted by F.

Preferably, the C1-C5alkyl is methyl.

Preferably, the C1-C5alkyl is substituted by F, for example trifluoromethyl.

Preferably, the C1-C5alkoxy is methoxy.

Preferably, the halogens represented by $R_1$, $R_2$, $R_3$, $R_4$ and $R_5$ are Cl or F.

In formula I, when n₁ is 1 or 2, and n₂ is 3 or 4, then $R_1$ and $R_2$ are selected from the group consisting of H, halogen or C1-C5alkyl, preferably H, Cl or methyl.

In formula I, when Ar has the formula II, then X is N, and $R_3$ or $R_4$ is selected from the group consisting of H, halogen, C1-C5alkyl, C1-C5alkyl substituted by halogen, C1-C5alkoxy and C1-C5alkoxy substituted by halogen. Preferably, $R_3$ or $R_4$ is selected from the group consisting of H, Cl, F, methyl, trifluoromethyl or methoxy.

In formula I, when Ar has the formula III, then Q is preferably O or S, and X is selected from the group consisting of N or CH, and $R_5$ is selected from the group consisting of H or halogen, preferably H or F.

Preferably, the above alicyclic[c]benzopyrone derivatives are the following compounds or the salts thereof:

(1) 7-{3-[4-(2,3-dimethylphenyl)piperazin-1-yl]-propoxy}-2,3-dihydro-1H-cyclopenteno[c]benzopyran-4-one,
(2) 7-{3-[4-(2,3-dichlorophenyl)piperazin-1-yl]-propoxy}-2,3-dihydro-1H-cyclopenteno[c]benzopyran-4-one,
(3) 7-{3-[4-(3-trifluoromethylphenyl)piperazin-1-yl]-propoxy}-2,3-dihydro-1H-cyclopenteno[c]benzopyran-4-one,
(4) 7-{3-[4-(2-methoxyphenyl)piperazin-1-yl]-propoxy}-2,3-dihydro-1H-cyclopenteno[c]benzopyran-4-one,
(5) 7-{3-[4-(3-(6-fluoro-benzisoxazole)-1-piperidyl)-n-propoxy]}-2,3-dihydro-1H-cyclopenteno[c]benzopyran-4-one,
(6) 7-{3-[4-(2-methoxyphenyl)piperazin-1-yl]-propoxy}-6-methyl-2,3-dihydro-1H-cyclopenteno[c]benzopyran-4-one,
(7) 7-{4-[4-(2-methoxyphenyl)piperazin-1-yl]-butoxy}-2,3-dihydro-1H-cyclopenteno[c]benzopyran-4-one,
(8) 7-{4-[4-(4-methoxyphenyl)piperazin-1-yl]-butoxy}-2,3-dihydro-1H-cyclopenteno[c]benzopyran-4-one,
(9) 7-{4-[4-(4-fluorophenyl)piperazin-1-yl]-butoxy}-2,3-dihydro-1H-cyclopenteno[c]benzopyran-4-one,
(10) 7-{4-[4-(3-(6-fluoro-benzisoxazole)-1-piperidyl)-butoxy]}-2,3-dihydro-1H-cyclopenteno[c]benzopyran-4-one,
(11) 7-{4-[4-(2-methoxyphenyl)piperazin-1-yl]-butoxy}-6-methyl-2,3-dihydro-1H-cyclopenteno[c]benzopyran-4-one,
(12) 7-{4-[4-(3-(1,2-benzisothiazole)-1-piperazinyl)-butoxy]}-6-methyl-2,3-dihydro-1H-cyclopenteno[c]benzopyran-4-one,
(13) 7-{4-[4-(2-methoxyphenyl)piperazin-1-yl]-butoxy}-6-chloro-2,3-dihydro-1H-cyclopenteno[c]benzopyran-4-one,
(14) 7-{4-[4-(3-(1,2-benzisothiazole)-1-piperazinyl)-n-butoxy]}-6-chloro-2,3-dihydro-1H-cyclopenteno[c]benzopyran-4-one,
(15) 7-{4-[4-(3-(6-fluoro-benzisoxazole)-1-piperidyl)-butoxy]}-6-chloro-2,3-dihydro-1H-cyclopenteno[c]benzopyran-4-one,
(16) 7-{4-[4-(3-(6-fluoro-benzisoxazole)-1-piperidyl)-butoxy]}-8-chloro-2,3-dihydro-1H-cyclopenteno[c]benzopyran-4-one,
(17) 7-{4-[4-(2-methoxyphenyl)piperazin-1-yl-butoxy]}-8-chloro-2,3-dihydro-1H-cyclopenteno[c]benzopyran-4-one,
(18) 3-{4-[4-(3-(6-fluoro-benzisoxazole)-1-piperidyl)-butoxy]}-7,8,9,10-tetrahydrobenzo[c]benzopyran-6-one,
(19) 3-{4-[4-(2-methoxyphenyl)piperazin-1-yl]-butoxy}-7,8,9,10-tetrahydrobenzo[c]benzopyran-6-one,
(20) 3-{4-[4-(2-methoxyphenyl)piperazin-1-yl]-butoxy}-4-methyl-7,8,9,10-tetrahydrobenzo[c]benzopyran-6-one, or
(21) 3-{4-[4-(3-(6-fluoro-benzisoxazole)-1-piperidyl)-butoxy]}-4-methyl-7,8,9,10-tetrahydrobenzo[c]benzopyran-6-one.

It is an other object of the invention to provide a pharmaceutical composition comprising the compound according to the invention for use in the treatment or prevention of central nervous system diseases.

It is another object of the invention to provide use of the compound according to the invention in the manufacture of a medicament for the treatment or prevention of central nervous system diseases.

It is another object of the invention to provide a method for treating or preventing central nervous system diseases, comprising administrating the compound according to the invention.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

All the documents cited in the present application are incorporated herein by reference in entirety. Unless otherwise stated, the ranges used herein indicating quantities, concentrations, components and compounds groups should be understood to encompass all the possible sub-ranges, and said ranges include their end values and all the integers and fractions therein.

Unless otherwise stated, all technical and scientific terms used herein have the same meaning as are commonly understood by a person skilled in the art to which the invention belong. The following definitions are provided for the purpose of better understanding of the invention. In the event that there is a conflict with the commonly understood meaning, those provided herein prevail.

Unless otherwise stated, the term "C1-C5alkyl" as used herein refers to a linear or branched alkyl containing 1-5 carbon atoms. The example includes methyl, ethyl, propyl, isopropyl, butyl, sec-butyl, t-butyl, n-pentyl, isopentyl, neopentyl or the like.

Unless otherwise stated, the term "C1-C5alkoxy" as used herein refers to a linear or branched alkyl containing 1-5 carbon atoms, which is attached to the parent structure via an oxygen atom. The example includes methoxy, ethoxy, propoxy, isopropoxy, butoxy, pentyloxy or the like.

Unless otherwise stated, the term "halogen" as used herein refers to F (fluorine), Cl (chlorine), Br (bromine) or I (iodine).

Said salt is a salt containing a pharmaceutically acceptable anion, for example, hydrochloride, hydrobromide, hydriodate, nitrate, sulfate or bisulfate, phosphate or acid phosphate, acetate, lactate, citrate, tartrate, maleate, fumarate, mesylate, gluconate, saccharate, benzoate, ethanesulfonate, benzenesulfonate, p-toluenesulfonate or the like.

The process for preparing the alicyclic[c]benzopyrone derivative comprises the following steps:

first synthesizing the parent structure of alicyclic[c]benzopyrone, which is then attached to 1,2-benzisoxazole or 1,2-benzisothiazole substituted by a piperazinyl or a piperidyl group via a carbon chain. The reaction is shown as follows:

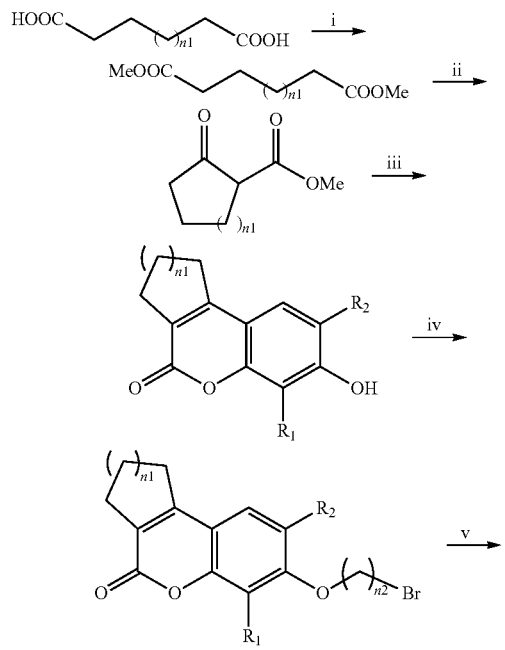

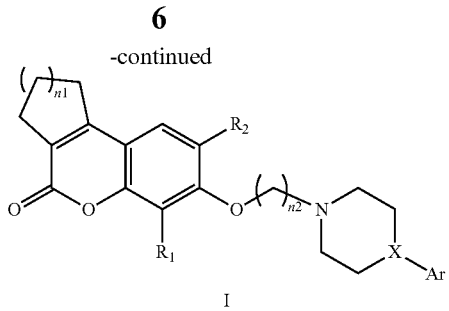

I

In step (i), the aliphatic dicarboxylic acid of formula

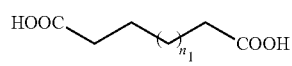

is reacted with anhydrous methanol under reflux according to the process known in the art, for example, with concentrated sulfuric acid to give the corresponding diester derivative.

In step (ii), at about 0° C., the resulting diester derivative is reacted under the action of a Lewis acid, such as anhydrous aluminum trichloride, in an organic solvent such as dichloromethane, which is then reacted in an organic base such as triethylamine.

In step (iii), the oxonaphthenic acid methyl ester compound is reacted with a resorcinol derivative in the presence of a reagent such as bismuth nitrate pentahydrate at the temperature of about 80° C.

In step (iv), the product from step (iii) is reacted with alkyl dihalide, such as 1,3-dibromopropane or 1,4-dibromobutane, in the presence of a base such as anhydrous potassium carbonate in an organic solvent such as acetone under reflux.

In step (v), the product from step (iv) is reacted with an aryl piperazine or piperidine derivative in organic solvent such as acetonitrile in the presence of a base such as anhydrous potassium carbonate and a catalyst such as potassium iodide under reflux to give the compound of formula I.

In the reaction formula, $n_1$, $n_2$, X, Ar, Q, $R_1$, $R_2$ and $R_3$ are defined as above.

The invention also relates to a pharmaceutical composition, comprising the compound of formula (I) or the pharmaceutically acceptable salt thereof in a therapeutically and prophylactically effective amount, and pharmaceutically acceptable carrier. The carrier includes but not limited to commonly used carrier substances, for example flavor, sweetener, liquid or solid filler, diluent or the like. The composition may be formulated into a conventional pharmaceutical formulation, including but not limited to tablet, capsule, powder, syrup, solution, suspension or injectable according to the process known in the art. The formulation usually contains the active ingredient in 1-99% by weight.

It is shown in an in vitro assay that the compounds according to the invention have relatively higher affinities for dopamine $D_2$, $D_3$, $5-HT_{1A}$ and $5-HT_{2A}$ receptors, while lower affinities for $5-HT_{2C}$. It is shown that the compounds according to the invention can significantly improve the MK-801 induced high activity and effectively improve the apomorphine induced clambering symptoms without causing EPS at effective dosage. Since these in vitro acting targets and in vivo pharmacological models are closely associated with dopamine function disorder induced neural system diseases, particularly schizophrenia, it is indicated that the compounds according to the invention have a therapeutic or prophylactic effect for central nervous system diseases, especially a therapeutic effect for schizophrenia. The compounds according to the invention may also be used to prepare a medicament for the treatment or prevention of central nervous system diseases, including mental disorder, anxiety, personality disorder, depression, mania, migraine, epilepsy or spasticity disorder, childhood disorder, Parkinson's disease, cognitive disorder, neural degeneration, neurotoxicity and ischemia, depression, memory disorder and functional disorders associated with intelligence, learning or the like, preferably schizophrenia.

The compounds according to the invention may be administrated to a patient in need thereof orally or intravenously, at a dosage of 0.001-30 mg/kg body weight per day, which may be determined by a physician according to age, condition or the like of the patient.

The compounds of formula I are development and improvement of benzopyrone derivatives described in Chinese Patent Application No. 201110086701.8. The preferable compounds according to the invention have higher affinities for $D_2$, $D_3$, $5HT_{1A}$ and $5HT_{2A}$ receptors, while lower affinities for $5HT_{2C}$, as well as lower $ED_{50}$ and higher potency in the two animal models in respect of MK-801 induced high activity and the apomorphine induced clambering, and lower $ED_{50}$ and greater therapeutical indices in animal catalepsy model. The results of the comparison of animal models and the in vitro receptor assay are listed in Table 5 and Table 6, respectively.

EXAMPLES

Generally, the compounds according to the invention may be prepared according to the process above or the variants thereof using available starting materials, reagent and conventional synthesis procedures. The reaction may be carried out in other manners known in the art but not mentioned herein. The starting materials are commercially available or synthesized according to the Examples, or available according to the processes known to a person skilled in the art.

The following Examples are provided for illustrative purpose for the invention rather than the limitation thereto.

Example 1

7-{3-[4-(2,3-dimethylphenyl)piperazin-1-yl]-propoxy}-2,3-dihydro-1H-cyclopenteno[c]benzopyran-4-one 1) 7.3 g of adipic acid (50 mmol) and 40 ml of anhydrous methanol were added to a flask, and 2 ml of concentrated sulfuric acid was added slowly and dropwise under stirring with heating, and the reaction was carried out under reflux for 5 hours. The mixture was cooled to room temperature and the solvent was distilled off under reduced pressure. The mixture was then diluted with 30 ml of dichloromethane and 25 ml of water. The aqueous layer was extracted with dichloromethane (30 ml×2). The organic layers were combined, and washed to neutral with saturated sodium bicarbonate solution and then with saturated NaCl, dried with anhydrous magnesium sulfate, and filtrated. The solvent was distilled off under reduced pressure to give 8 g of dimethyl adipate. The yield was 91.9%.

2) 8.7 g (50 mmol) of dimethyl adipate, anhydrous aluminum trichloride (20 g) and 100 ml of dry dichloromethane were cooled to 0° C. under an ice bath. At 0° C., triethylamine (dried with sodium hydroxide, 45 ml) was added dropwise and slowly. After addition, the ice bath was removed and the reaction was carried out at room temperature for 4 hours, being monitored with TLC. After the reaction was completed, the reaction liquid was poured into an ice-water mixture slowly, which was stirred for 30 min. The organic layer was separated and the aqueous layer was extracted with dichloromethane (50 ml×2). The organic layers were combined and washed with water and then with saturated NaCl, dried with anhydrous magnesium sulfate, and filtrated. The solvent was distilled off under reduced pressure to give 5.1 g of 2-oxocyclopentanecarboxylate methyl ester. The yield was 71.8%.

3) 7.1 g (50 mmol) of 2-oxocyclopentanecarboxylate methyl ester, 5.5 g (50 mmol) of resorcinol and bismuth nitrate pentahydrate were heated to 80° C. and the reaction was carried out for 4 hours. After the reaction was completed, the reaction mixture was cooled to room temperature and the reaction liquid was poured into water and yellowish solid was precipitated. Stirring was performed for 30 min and filtration lead to solid. Recrystallization with 95% ethanol gave 5.8 g of white solid. The yield was 57.4%.

4) 5 g of the product from step 3), 6 g of anhydrous potassium carbonate, 50 ml of acetone and 8 g of 1,3-dibromopropane were heated under reflux for 6 hours and then cooled to room temperature and filtrated. The solvent was distilled off to give yellowish oil, which was pass through a column to give 5 g of white solid.

5) To 0.51 g of the product from step 4) was added 0.61 g of 2,3-dimethylphenylpiperazine hydrochloride, 2 g of anhydrous potassium carbonate, 0.2 g of potassium iodide and 25 ml of acetonitrile and the mixture was heated under reflux for 12 hours and then cooled to room temperature. The solvent was distilled off. Appropriate amount of dichloromethane was added to the reaction mixture, which was washed with water. The aqueous layer was separated and the organic layer was dried with anhydrous magnesium sulfate. The solvent was distilled off to give yellowish oil, which was pass through a chromatograph column to give 0.48 g of white solid.

$^1$H NMR (CDCl$_3$) δ 2.03-2.26 (m, 10H), 2.59-2.66 (m, 6H), 2.89-3.04 (m, 8H), 4.11 (t, 2H, J=12.8 Hz), 6.84-6.94 (m, 4H), 7.06-7.08 (m, 1H), 7.33 (d, 1H, J=8.4 Hz)

MS (ESI) m/z 433.3 ([M+H]$^+$).

Example 2

7-{3-[4-(2,3-dichlorophenyl)piperazin-1-yl]-propoxy}-2,3-dihydro-1H-cyclopenteno[c]benzopyran-4-one The target compound was prepared according to the procedures of Example 1, using 2,3-dichlorophenylpiperazine hydrochloride instead of 2,3-dimethylphenylpiperazine hydrochloride.

$^1$H NMR (CDCl$_3$) δ 2.03-2.23 (m, 4H), 2.60-2.68 (m, 6H), 2.89 (t, 2H, J=15.2 Hz), 3.02-3.08 (m, 6H), 4.11 (t, 2H, J=12.4 Hz), 6.84-6.98 (m, 3H), 7.14-7.16 (m, 2H), 7.33 (d, 1H, J=8.4 Hz)

MS (ESI) m/z 473.2 ([M+H]$^+$).

Example 3

7-{3-[4-(3-trifluoromethylphenyl)piperazin-1-yl]-propoxy}-2,3-dihydro-1H-cyclopenteno[c]benzopyran-4-one The target compound was prepared according to the procedures of Example 1, using 3-trifluoromethylphenylpiperazine hydrochloride instead of 2,3-dimethylphenylpiperazine hydrochloride.

$^1$H NMR (CDCl$_3$) δ 2.03-2.23 (m, 4H), 2.59-2.66 (m, 6H), 2.89 (t, 2H, J=14.8 Hz), 3.04 (t, 2H, J=15.8 Hz), 3.26 (t, 4H,

J=10 Hz), 4.11 (t, 2H, J=12.4 Hz), 6.84-6.87 (m, 2H), 7.06-7.11 (m, 3H), 7.32-7.34 (m, 2H)

MS (ESI) m/z 473.3 ([M+H]$^+$).

Example 4

7-{3-[4-(2-methoxy)piperazin-1-yl]-propoxy}-2,3-dihydro-1H-cyclopenteno[c]benzopyran-4-one The target compound was prepared according to the procedures of Example 1, using 2-methoxyphenylpiperazine hydrochloride instead of 2,3-dimethylphenyl piperazine hydrochloride.

$^1$H NMR (CDCl$_3$) δ 2.05-2.21 (m, 4H), 2.62 (t, 2H, J=14.4 Hz), 2.70 (s, br, 4H), 2.87-2.89 (m, 2H), 3.02-3.12 (m, 6H), 3.87 (s, 3H), 4.10 (t, 2H, J=12.4 Hz), 6.84-7.00 (m, 6H), 7.32-7.34 (m, 1H)

MS (ESI) m/z 435.3 ([M+H]$^+$).

Example 5

7-{3-[4-(3-(6-fluoro-benzisoxazole)-1-piperidyl)-n-propoxy]}-2,3-dihydro-1H-cyclopenteno[c]benzopyran-4-one The target compound was prepared according to the procedures of Example 1, using 6-fluoro-3-(4-piperidyl)-1,2-benzisoxazole hydrochloride instead of 2,3-dimethylphenyl piperazine hydrochloride.

$^1$H NMR (CDCl$_3$) δ 1.90-2.20 (m, 10H), 2.61 (t, 2H, J=14.8 Hz), 2.88-2.91 (m, 2H), 3.03-3.11 (m, 5H), 4.11 (t, 2H, J=12.4 Hz), 6.85-6.87 (m, 2H), 7.06-7.07 (m, 1H), 7.23-7.35 (m, 2H), 7.70-7.73 (m, 1H)

MS (ESI) m/z 463.3 ([M+H]$^+$).

Example 6

7-{3-[4-(2-methoxyphenyl)piperazin-1-yl]-propoxy}-6-methyl-2,3-dihydro-1H-cyclopenteno[c]benzopyran-4-one The target compound was prepared according to the procedures of Example 4, using 2-methylresorcinol as starting material.

$^1$H NMR (CDCl$_3$) δ 2.06-2.21 (m, 4H), 2.33 (s, 3H), 2.65-3.12 (m, 14H), 3.87 (s, 3H), 4.13 (t, 2H, J=12.8 Hz), 6.83-7.01 (m, 5H), 7.22-7.27 (m, 1H)

MS (ESI) m/z 449.3 ([M+H]$^+$)

Example 7

7-{4-[4-(2-methoxyphenyl)piperazin-1-yl]-butoxy}-2,3-dihydro-1H-cyclopenteno[c]benzopyran-4-one The target compound was prepared according to the procedures of Example 4, using 1,4-dibromobutane instead of 1,3-dibromopropane.

$^1$H NMR (CDCl$_3$) δ 1.74-1.89 (m, 4H), 2.19-2.21 (m, 3H), 2.52 (t, 2H, J=14.4 Hz), 2.71 (s, br, 4H), 2.87-2.90 (m, 2H), 3.02-3.13 (m, 5H), 3.86 (s, 3H), 4.05 (t, 2H, J=12.4 Hz), 6.83-7.00 (m, 6H), 7.32-7.34 (m, 4H)

MS (ESI) m/z 449.3 ([M+H]$^+$)

Example 8

7-{4-[4-(4-methoxyphenyl)piperazin-1-yl]-butoxy}-2,3-dihydro-1H-cyclopenteno[c]benzopyran-4-one The target compound was prepared according to the procedures of Example 7, using 4-methoxyphenylpiperazine hydrochloride instead of 2-methoxyphenylpiperazine hydrochloride.

$^1$H NMR (CDCl$_3$) δ 1.71-1.87 (m, 4H), 2.19 (t, 2H, J=14.8 Hz), 2.47 (t, 2H, J=14.8 Hz), 2.62-2.64 (m, 4H), (t, 4H, J=10 Hz), 2.89 (t, 2H J=15.2 Hz), 3.04 (t, 2H, J=15.2 Hz), 3.09-3.11 (m, 4H), 3.77 (s, 3H), 4.05 (t, 2H, J=12.4 Hz), 6.82-6.92 (m, 6H), 7.32 (d, 1H, J=8.4 Hz)

MS (ESI) m/z 449.3 ([M+H]$^+$)

Example 9

7-{4-[4-(4-fluorophenyl)piperazin-1-yl]-butoxy}-2,3-dihydro-1H-cyclopenteno[c]benzopyran-4-one The target compound was prepared according to the procedures of Example 7, using 4-fluorophenylpiperazine hydrochloride instead of 2-methoxyphenylpiperazine hydrochloride.

$^1$H NMR (CDCl$_3$) δ 1.71-1.89 (m, 4H), 2.19 (t, 2H, J=15.2 Hz), 2.47 (t, 2H, J=14.8 Hz), 2.62 (t, 4H, J=10 Hz), 2.88 (t, 2H, J=14.8 Hz), 3.03 (t, 2H, J=15.2 Hz), 3.12 (t, 2H, J=9.6 Hz), 4.05 (t, 2H, J=12.4 Hz), 6.82-6.97 (m, 6H), 7.32 (d, 1H, J=9.2 Hz)

MS (ESI) m/z 437.2 ([M+H]$^+$)

Example 10

7-{4-[4-(3-(6-fluoro-benzisoxazole)-1-piperidyl)-butoxy]}-2,3-dihydro-1H-cyclopenteno[c]benzopyran-4-one The target compound was prepared according to the procedures of Example 7, using 6-fluoro-3-(4-piperidyl)-1,2-benzisoxazole hydrochloride instead of 2-methoxyphenylpiperazine hydrochloride.

$^1$H NMR (CDCl$_3$) δ 1.74-1.88 (m, 4H), 2.06-2.21 (m, 8H), 2.48 (t, 2H, J=14.8 Hz), 2.87-2.89 (m, 2H), 3.02-3.10 (m, 5H), 4.06 (t, 2H, J=12.4 Hz), 6.83-6.86 (m, 2H), 7.04-7.05 (m, 1H), 7.22-7.27 (m, 1H), 7.33 (d, 1H, J=9.2 Hz), 7.68-7.71 (m, 1H)

MS (ESI) m/z 477.3 ([M+H]$^+$)

Example 11

7-{4-[4-(2-methoxyphenyl)piperazin-1-yl]-butoxy}-6-methyl-2,3-dihydro-1H-cyclopenteno[c]benzopyran-4-one The target compound was prepared according to the procedures of Example 6, using 1,4-dibromobutane instead of 1,3-dibromopropane.

$^1$H NMR (CDCl$_3$) δ 1.76-1.90 (m, 4H), 2.16-2.20 (m, 2H), 2.33 (s, 3H), 2.51 (t, 2H, J=14.8 Hz), 2.67 (s, br, 4H), 2.87-2.90 (m, 2H), 3.00-3.10 (m, 5H), 3.86 (s, 3H), 4.08 (t, 2H, J=12 Hz), 6.80-6.99 (m, 5H), 7.21-7.23 (m, 1H)

MS (ESI) m/z 463.3 ([M+H]$^+$)

Example 12

7-{4-[4-(3-(1,2-benzisothiazole)-1-piperazinyl)-butoxy]}-6-methyl-2,3-dihydro-1H-cyclopenteno[c]benzopyran-4-one

The target compound was prepared according to the procedures of Example 11, using 3-(1-piperazinyl)-1,2-benzisothiazole hydrochloride instead of 2-methoxyphenylpiperazine hydrochloride.

$^1$H NMR (CDCl$_3$) δ 1.78-1.92 (m, 4H), 2.17-2.21 (m, 2H), 2.34 (s, 3H), 2.54 (t, 2H, J=14.4 Hz), 2.69-2.72 (m, 4H), 2.89-3.03 (m, 4H), 3.57-3.59 (m, 4H), 4.10 (t, 2H, J=12.4 Hz), 6.81-6.83 (m, 1H), 7.22-7.27 (m, 1H), 7.34-7.37 (m, 1H), 7.45-7.49 (m, 1H), 7.80-7.82 (m, 1H), 7.90-7.92 (m, 1H)

MS (ESI) m/z 490.3 ([M+H]$^+$)

Example 13

7-{4-[4-(2-methoxyphenyl)piperazin-1-yl]-butoxy}-6-chloro-2,3-dihydro-1H-cyclopenteno[c]benzopyran-4-one

The target compound was prepared according to the procedures of Example 11, using 2-chlororesorcinol instead of 2-methylresorcinol.

$^1$H NMR (CDCl$_3$) δ 1.78-1.96 (m, 4H), 2.18-2.22 (m, 2H), 2.51 (t, 2H, J=14.8 Hz), 2.67 (s, br, 4H), 2.87-2.90 (m, 2H), 3.01-3.10 (m, 5H), 3.86 (s, 3H), 4.16 (t, 2H, J=12.4 Hz), 6.87-6.93 (m, 5H), 7.26-7.28 (m, 1H)

MS (ESI) m/z 483.3 ([M+H]$^+$)

Example 14

7-{4-[4-(3-(1,2-benzisothiazole)-1-piperazinyl)-n-butoxy]}-6-chloro-2,3-dihydro-1H-cyclopenteno[c]benzopyran-4-one

The target compound was prepared according to the procedures of Example 13, using 3-(1-piperazinyl)-1,2-benzisothiazole hydrochloride instead of 2-methoxyphenylpiperazine hydrochloride.

$^1$H NMR (CDCl$_3$) δ 1.76-2.20 (m, 6H), 2.54 (t, 2H, J=14.4 Hz), 2.68-2.70 (m, 4H), 2.85-2.99 (m, 2H), 3.01-3.03 (m, 2H), 3.55 (s, br, 4H), 4.17 (t, 2H, J=12 Hz), 6.85-6.88 (m, 1H), 7.24-7.36 (m, 2H), 7.43-7.47 (m, 1H), 7.77-7.80 (m, 1H), 7.88-7.91 (m, 1H)

MS (ESI) m/z 510.2 ([M+H]$^+$)

Example 15

7-{4-[4-(3-(6-fluoro-benzisoxazole)-1-piperidyl)-butoxy]}-6-chloro-2,3-dihydro-1H-cyclopenteno[c]benzopyran-4-one

The target compound was prepared according to the procedures of Example 13, using 6-fluoro-3-(4-piperidyl)-1,2-benzisoxazole hydrochloride instead of 2-methoxyphenylpiperazine hydrochloride.

$^1$H NMR (CDCl$_1$) δ 1.76-2.23 (m, 12H), 2.51 (t, 2H, J=14.8 Hz), 2.87-2.90 (m, 2H), 3.02-3.11 (m, 5H), 4.17 (t, 2H, J=12.4 Hz), 6.88-6.91 (m, 1H), 7.04-7.05 (m, 1H), 7.22-7.30 (m, 2H), 7.68-7.72 (m, 1H)

MS (ESI) m/z 511.3 ([M+H]$^+$)

Example 16

7-{4-[4-(3-(6-fluoro-benzisoxazole)-1-piperidyl)-butoxy]}-8-chloro-2,3-dihydro-1H-cyclopenteno[c]benzopyran-4-one

The target compound was prepared according to the procedures of Example 15, using 4-chlororesorcinol instead of 2-chlororesorcinol as starting material.

$^1$H NMR (CDCl$_3$) δ 1.79-2.23 (m, 12H), 2.51 (t, 2H, J=14.4 Hz), 2.88-2.92 (m, 2H), 3.00-3.09 (m, 5H), 4.12 (t, 2H, J=12.4 Hz), 6.88-6.89 (m, 1H), 7.03-7.05 (m, 1H), 7.23-7.27 (m, 1H), 7.42 (s, 1H), 7.68-7.72 (m, 1H)

MS (ESI) m/z 511.3 ([M+H]$^+$)

Example 17

7-{4-[4-(2-methoxyphenyl)piperazin-1-yl-butoxy]}-8-chloro-2,3-dihydro-1H-cyclopenteno[c]benzopyran-4-one

The target compound was prepared according to the procedures of Example 16, using 2-methoxyphenylpiperazine hydrochloride instead of 6-fluoro-3-(4-piperidyl)-1,2-benzisoxazole hydrochloride.

$^1$H NMR (CDCl$_3$) δ 1.69-1.95 (m, 6H), 2.19-2.23 (m, 2H) 2.51 (t, 2H, J=14.8 Hz), 2.68 (s, br, 3H), 2.88-2.91 (m, 2H), 3.00-3.10 (m, 5H), 3.86 (s, 3H) 4.12 (t, 2H, J=12.4 Hz), 6.85-7.00 (m, 5H), 7.41 (s, 1H)

MS (ESI) m/z 483.3 ([M+H]$^+$)

Example 18

3-{4-[4-(3-(6-fluoro-benzisoxazole)-1-piperidyl)-butoxy]}-7,8,9,10-tetrahydrobenzo[c]benzopyran-6-one

The target compound was prepared according to the procedures of Example 10, using pimelic acid instead of adipic acid.

$^1$H NMR (CDCl$_1$) δ 1.67-1.87 (m, 10H), 2.06-2.13 (m, 4H), 2.47 (t, 2H, J=14.8 Hz), 2.56 (t, 2H, J=8.8 Hz), 2.75 (t, 2H, J=8.8 Hz), 3.07-3.10 (m, 3H), 4.05 (t, 2H, J=12.8 Hz), 6.80-6.85 (m, 2H), 7.04-7.05 (m, 1H), 7.22-7.25 (m, 1H), 7.45 (d, 1H, J=8.4 Hz), 7.68-7.71 (m, 1H)

MS (ESI) m/z 491.3 ([M+H]$^+$)

Example 19

3-{4-[4-(2-methoxyphenyl)piperazin-1-yl]-butoxy}-7,8,9,10-tetrahydrobenzo[c]benzopyran-6-one

The target compound was prepared according to the procedures of Example 18, using 2-methoxyphenyl piperazine hydrochloride instead of 6-fluoro-3-(4-piperidyl)-1,2-benzisoxazole hydrochloride.

$^1$H NMR (CDCl$_3$) δ 1.73-1.87 (m, 8H), 2.47-2.74 (m, 10H), 3.11 (s, br, 4H), 3.86 (s, 3H) 4.04 (t, 2H, J=12.4 Hz), 6.78-6.99 (m, 6H), 7.43-7.15 (m, 1H)

MS (ESI) m/z 463.3 ([M+H]$^+$)

Example 20

3-{4-[4-(2-methoxyphenyl)piperazin-1-yl]-butoxy}-4-methyl-7,8,9,10-tetrahydrobenzo[c]benzopyran-6-one The target compound was prepared according to the procedures of Example 19, using 2-methylresorcinol instead of resorcinol.

$^1$H NMR (CDCl$_3$) δ 1.76-1.88 (m, 8H), 2.32 (s, 3H), 2.48-2.75 (m, 10H), 3.11 (s, br, 4H), 3.87 (s, 3H), 4.08 (t, 2H, J=12.4 Hz), 6.80-7.00 (m, 5H), 7.35 (d, 1H, J=8.8 Hz)

MS (ESI) m/z 477.3 ([M+H]$^+$)

Example 21

3-{4-[4-(3-(6-fluoro-benzisoxazole)-1-piperidyl)-butoxy]}-4-methyl-7,8,9,10-tetrahydrobenzo[c]benzopyran-6-one The target compound was prepared according to the procedures of Example 18, using 2-methylresorcinol instead of resorcinol as starting material.

$^1$H NMR (CDCl$_3$) δ 1.78-1.88 (m, 8H), 2.07-2.08 (m, 6H), 2.32 (s, 3H), 2.48 (t, 2H, J=7.6 Hz), 2.57-2.75 (m, 4H), 3.08-3.10 (m, 3H), 4.08 (t, 2H, J=12 Hz), 6.81-6.83 (m, 1H), 7.05-7.06 (m, 1H), 7.23-7.26 (m, 1H), 7.35-7.37 (m, 1H), 7.68-7.71 (m, 1H)

MS (ESI) m/z 505.3 ([M+H]$^+$)

TABLE 1

Numbering of the preferable compounds prepared in the Examples and their structure formulae and corresponding groups.

| No: | Structural Formula | $n_1$ | $n_2$ | X | Ar | Q | $R_1$ | $R_2$ | $R_3$ | $R_4$ | $R_5$ |
|---|---|---|---|---|---|---|---|---|---|---|---|
| 1 | | 1 | 3 | N | II | | H | H | | CH$_3$ | CH$_3$ |
| 2 | | 1 | 3 | N | II | | H | H | | Cl | Cl |
| 3 | | 1 | 3 | N | II | | H | H | | H | CF$_3$ |
| 4 | | 1 | 3 | N | II | | H | H | | OCH$_3$ | H |
| 5 | | 1 | 3 | CH | III | O | H | H | | | F |

TABLE 1-continued

Numbering of the preferable compounds prepared in the Examples and their structure formulae and corresponding groups.

| No: | Structural Formula | $n_1$ | $n_2$ | X | Ar | Q | $R_1$ | $R_2$ | $R_3$ | $R_4$ | $R_5$ |
|---|---|---|---|---|---|---|---|---|---|---|---|
| 6 | | 1 | 3 | N | II | | $CH_3$ | H | $OCH_3$ | H | |
| 7 | | 1 | 4 | N | II | | H | H | $OCH_3$ | H | |
| 8 | | 1 | 4 | N | II | | H | H | H | $OCH_3$ | |
| 9 | | 1 | 4 | N | II | | H | H | H | F | |
| 10 | | 1 | 4 | CH | III | O | H | H | | | F |
| 11 | | 1 | 4 | N | II | | $CH_3$ | H | $OCH_3$ | H | |
| 12 | | 1 | 4 | N | III | S | $CH_3$ | H | | | H |

TABLE 1-continued

Numbering of the preferable compounds prepared in the Examples and their structure formulae and corresponding groups.

| No: | Structural Formula | $n_1$ | $n_2$ | X | Ar | Q | $R_1$ | $R_2$ | $R_3$ | $R_4$ | $R_5$ |
|---|---|---|---|---|---|---|---|---|---|---|---|
| 13 | | 1 | 4 | N | II | | Cl | H | OCH$_3$ | | H |
| 14 | | 1 | 4 | N | III | S | Cl | H | | | H |
| 15 | | 1 | 4 | CH | III | O | Cl | H | | | F |
| 16 | | 1 | 4 | CH | III | O | H | Cl | | | F |
| 17 | | 1 | 4 | N | II | | H | Cl | OCH$_3$ | | H |
| 18 | | 2 | 4 | CH | III | O | H | H | | | F |
| 19 | | 2 | 4 | N | II | | H | H | OCH$_3$ | | H |

TABLE 1-continued

Numbering of the preferable compounds prepared in the Examples and their structure formulae and corresponding groups.

| No: | Structural Formula | $n_1$ | $n_2$ | X | Ar | Q | $R_1$ | $R_2$ | $R_3$ | $R_4$ | $R_5$ |
|---|---|---|---|---|---|---|---|---|---|---|---|
| 20 | 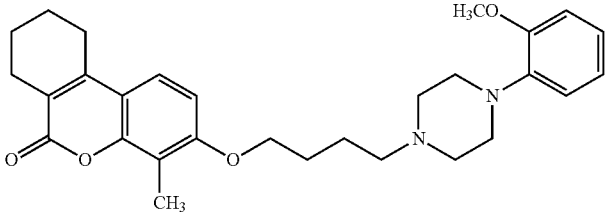 | 2 | 4 | N | II | | CH3 | H | OCH3 | H | |
| 21 | 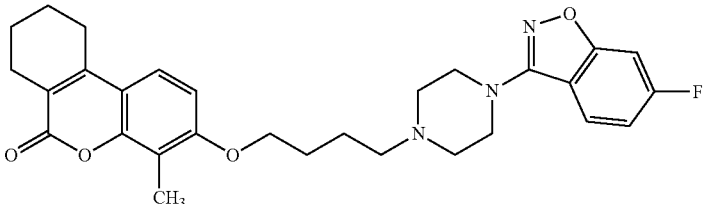 | 2 | 4 | CH | III | O | CH3 | H | | | F |

Example 22

5HT$_{1A}$ Receptor Assay

Preparation of 5HT$_{1A}$ Membrane

Rats were sacrificed by cervical dislocation on ice. Cerebral cortex was rapidly taken, and 2 cerebral cortexes were combined into a centrifuge tube, to which 3 ml of buffer (0.05 M Tris-HCl buffer, containing 0.1% ascorbic acid, 10 μm pargyline and 4 mM CaCl$_2$) was added. Homogenization was conducted for 3-4 s at level 4 for four times, and then 5 ml of buffer was added (0.05 M Tris-HCl buffer, containing 0.1% ascorbic acid, 10 μm pargyline and 4 mM CaCl$_2$). Incubation at 37° C. was conducted for 10 min, the weight of the tubes were adjusted using a balance after incubation. Centrifugation was conducted at 12000 r, 4° C. for 20 min, the supernatant was discarded, and 3 ml of buffer was added. Vortex mixer was used for blending, and then 5 ml of buffer was added. Centrifugation was conducted and repeated 3 times. After the centrifugations, the supernatant was discarded, and the pellets were stored at −80° C. for future use.

Materials for the Receptor Binding Assay

Isotope ligand $^3$H-8-OH-DPAT (67.0 Ci/mmol) was purchased from PerkinElmer Company; 5-HT was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of homogenized liquid were added into each reaction tube.

(3) 100 μL of homogenized liquid was added into the total binding tube (TB), 100 μL of 5-HT (final concentration 10$^{-5}$ M) was added into the non-specific binding tube (NB), and 100 μL of the test compound (final concentration 10$^{-5}$ M) was added into the specific binding tube (SB) for each compound.

(4) 10 μL of radioactive ligand $^3$H-8-OH-DPAT was respectively added into each reaction tube (2 parallel tubes were used for each reaction tube, and each of them was placed on ice when adding sample).

(5) Each reaction tube was incubated at 37° C. for 10 min; after the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate ($I$ %)=(Total binding tube cpm−compound cpm)/(Total binding tube cpm−non-specific binding tube cpm)×100%

Each assay for the compounds was conducted in duplicate. The results are listed in Table 2.

Example 23

5HT$_{2A}$ Receptor Assay

Preparation of 5HT$_4$ Membrane

Rats were sacrificed by cervical dislocation on ice. Cerebral cortex was rapidly taken, and 2 cerebral cortexes were combined into a centrifuge tube, to which 3 ml of buffer (0.05 M Tris-HCl buffer: 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after incubation. Centrifugation was conducted at 12000 r, 4° C. for 20 min, the supernatant was discarded, and 3 ml of A solution was added. Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-Ketanserin (67.0 Ci/mmol) was purchased from PerkinElmer Company; Methysergide was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of buffer, and homogenizer was used for evenly dispersing. 15 tubes were mixed into a 100 ml container, and appropriate amount of buffer was added to give 50 ml of membrane suspension, which was reserved for future use.

(2) 100 μL of membrane preparation and 100 μL of homogenized liquid were added into each reaction tube.

(3) 100 μL of homogenized liquid was added into the total binding tube (TB), 100 μL of Methysergide (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-Ketanserin was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate ($I$ %)=(Total binding tube cpm−compound cpm)/(Total binding tube cpm−non-specific binding tube cpm)×100%

Each assay for the compounds was conducted in duplicate. The results are listed in Table 2.

Example 24

D$_2$ Receptor Inhibition

Rats were sacrificed by cervical dislocation on ice. Cerebral cortex was rapidly taken, and 2 cerebral cortexes were combined into a centrifuge tube, to which 3 ml of buffer (0.05 M Tris-HCl buffer, containing NaCl 120 mM, KCl 5 mM, MgCl$_2$ 1 mM, CaCl$_2$ 1 mM) was added, homogenization was conducted for 3-4 s at level 4 for four times, and then 5 ml of buffer was then added. The weight of the homogenized tubes were adjusted using a balance, and centrifugation was conducted at 12000 r, 4° C. for 20 min. The supernatant was discarded, and 3 ml of B solution was added. Vortex mixer was used for blending, and then 5 ml of B solution was added. Centrifugation was conducted and repeated 3 times. After the centrifugations, the supernatant was discarded, and the pellets were stored at −80° C. for future use.

Materials for the Receptor Binding Assay

Isotope ligand $^3$H-Spiperone (67.0 Ci/mmol) was purchased from PerkinElmer Company; Butaclamol was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer were added into each reaction tube.

(3) 100 μL of homogenized liquid was added into the total binding tube (TB), 100 μL of Butaclamol (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand $^3$H-Spiperone was respectively added into each reaction tube (2 parallel tubes were used for each reaction tube, and each of them was placed on ice when adding sample).

(5) Each of the reaction tubes was incubated at 37° C. for 20 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibitory rate ($I$ %)=(Total binding tube cpm−compound cpm)/(Total binding tube cpm−non-specific binding tube cpm)×100%

Each assay for the compounds was conducted in duplicate. The results are listed in Table 2.

Example 25

D$_3$ Receptor Assay

Cell

In HEK-293 cells, after 48-72 hours, receptor proteins were expressed on membrane in large amount. After the cells were centrifuged at 1000 rpm for 5 min, the supernatant was discarded, and the cell pellet was collected and stored in a −20° C. fridge for reservation. It was re-suspended with Tris-Cl (pH 7.4) in the assay.

Materials for the Assay

D$_3$ receptor isotope ligand [3H]-Spiperone was purchased from Amersham Company; (+) Butaclamol was purchased from RBI Company; GF/C glass fiber filter paper was purchased from Whatman Company; lipid-soluble scintillation solution. Tris was divided into aliquots by Genetimes Technology Inc.

Procedures

Competitive binding test for receptors: 20 μl of each of the test compounds and 20 μl of the radioactive ligand together with 160 μl of the receptor proteins were added into the reaction tubes, and the final concentrations of the test compound and the positive drug were all 10 μmol/L. After 50 min of incubation in 30° C. water bath, the tubes were immediately moved to ice bath to terminate the reactions. GF/C glass fiber filter papers were used for rapid sucking filtration on a Millipore cell sample collector, elution buffer (50 mM Tris-HCl, PH 7.4) was applied for 3 ml×3 times, and microwave was applied for 4-5 min for drying. The filter papers were moved into 0.5 ml centrifuge tubes, and 500 μl of lipid-soluble scintillation solution was added. The tubes were allowed to stand still for over 30 min in dark, and the intensities of radioactivity were measured by a counter. The percentage inhibition rates of each compound against the binding of isotope ligands were calculated according to the following formula:

Inhibition rate ($I\%$)=(Total binding tube cpm−compound cpm)/(Total binding tube cpm−non-specific binding tube cpm)×100%

The results are listed in Table 2.

Example 26

5HT$_2$ Receptor Assay

Preparation of 5HT$_{2C}$ Membrane

Rats were sacrificed by cervical dislocation on ice. Cerebral cortex was rapidly taken, and 2 cerebral cortexes were combined into a centrifuge tube, to which 3 ml of buffer (0.05 M Tris-HCl buffer, 6.05 g of Tris was dissolved in 1000 ml of double-distilled water, and concentrated HCl was used to adjust to pH 7.5) was added, homogenization was conducted for 3-4 s at level 4 for four times, and then 5 ml of buffer was added. Incubation at 37° C. was conducted for 10 min, the weight of the tubes were adjusted using a balance after the incubation. Centrifugation was conducted at 12000 r, 4° C. for 20 min, the supernatant was discarded, and 3 ml of A solution was added. Vortex mixer was used for blending, and then 5 ml of buffer was added. Centrifugation was conducted (repeated 3 times). After the centrifugations, the supernatant was discarded, and the pellets were stored at −80° C. for future use.

Materials for the Receptor Binding Assay

Isotope ligand [$^3$H]-mesulergine (67.0 Ci/mmol) was purchased from PerkinElmer Company; mianserin was purchased from RBI Company; GF/C glass fiber filter paper was purchased from Whatman Company; Tris was imported and divided into aliquots; PPO, POPOP were purchased from Shanghai No. 1 Reagent Factory; lipid-soluble scintillation solution. Beckman LS-6500 Multi-function Liquid Scintillation Counter was used.

Procedures (1) The prepared membrane was first applied with appropriate amount of homogenized liquid, and homogenizer was used for evenly dispersing. 15 tubes were mixed into a 100 ml container, and appropriate amount of homogenized liquid was added to give 50 ml of membrane suspension, which was reserved for future use.

(2) 100 μL of membrane preparation and 100 μL of buffer were added into each reaction tube.

(3) 100 μL of homogenized liquid was added into the total binding tube (TB), 100 μL of mianserin (final concentration $10^{-5}$ M) was added into the non-specific binding tube (NB), and 100 μL of the test compound (final concentration $10^{-5}$ M) was added into the specific binding tube (SB) for each compound.

(4) 10 μL of radioactive ligand [$^3$H]-mesulergine was respectively added into each reaction tube (2 parallel tubes were used for each reaction tube, and each of them was placed on ice when adding sample).

(5) Each of the reaction tubes was incubated at 37° C. for 15 min. After the reaction was completed, the bound ligands were rapidly filtered under reduced pressure, and the ice-chilled assay buffer was used for adequate washing. The filter was taken out and put into a 3 ml scintillation vial, and 2 ml of toluene scintillation solution was added and blended.

(6) The scintillation vials were put into Liquid Scintillation Counter for counting.

Inhibition rate ($I\%$)=(Total binding tube cpm−compound cpm)/(Total binding tube cpm−non-specific binding tube cpm)×100%

Each assay for the compounds was conducted in duplicate. The results are listed in Table 2.

The results of in vitro assay indicate that compound 7 has relatively stronger affinities for four receptors (D$_2$, D$_3$, 5-HT$_{1A}$ and 5-HT$_{2A}$), while lower affinity for 5HT$_{2C}$.

Example 27

MK-801 Induced High Activity—the In Vivo Anti-Schizophrenia Activity of the Compounds Animals and Reagents Healthy mice of Kunming breed (with half male and half female, (20±2) g) were provided by Qinglongshan Animal Cultivation Center, Nanjing.

Ascorbic acid was provided by Sinopharm Chemical Reagent Co. Ltd.

MK-801 was produced by Sigma Company, USA; the formulation method: 0.1% vitamin C was used to formulate a 1 mg/ml solution.

Test positive drugs: haloperidol, clozapine, risperidone, olanzapine, aripiprazole, ziprasidone, quetiapine.

Tween 80, with the concentration of 10%.

Procedures

Mice with qualified body weight were selected, and randomly divided into blank group, model group, positive control group (risperidone group) and drug group. 10% Tween was administered intragastrically to the blank group and the model group at 0.1 ml/10 g; risperidone was administered intragastrically to the positive control group at 0.1 mg/kg; and corresponding amounts of drugs were administered intragastrically to the drug groups, respectively. 1 h after the administration, 0.1% of ascorbic acid was intraperitoneally injected to the blank group at 0.1 ml/10 g; and the model group, the positive control group (30 min) and the drug groups were intraperitoneally injected the MK-801 solution at 0.1 mg/kg. Subsequently, the spontaneous activities of the mice of each group in 90 min were measured.

The results are listed in Table 3.

The results of this assay indicate that, when compared to the model group, risperidone, compound 7 can not only significantly improve the MK-801 induced high activity, but also effectively improve the apomorphine induced clambering symptoms, and they did not cause EPS at effective dosage, indicating that they have notable anti-schizophrenia effects.

Example 28

Apomorphine Induced Clambering Assay of Mice

Animals

Healthy KM mice (male, with body weight of 18-22 g) were provided by Qinglongshan Animal Cultivation Center, Nanjing.

Main Reagents

Test positive drugs: haloperidol, clozapine, risperidone, olanzapine, aripiprazole, ziprasidone, quetiapine.

Apomorphine provided by Sigma Company was dissolved in 0.9% NaCl (containing 0.1% vitamin C) before use, and was freshly formulated before use.

Vitamin C, F20061113, was provided by Sinopharm Chemical Reagent Co. Ltd.

Sodium chloride injection, H32026305, was provided by Xuzhou No. 5 Pharmaceutical Factory Co. Ltd.

Instruments: self-made clambering cage, chronograph.

Procedures: apomorphine induced clambering assay of mice

KM mice (male, with body weight of 18-22 g) were randomly divided into negative control group, model group, positive drug groups for each dosage (risperidone, aripiprazole, ziprasidone, quetiapine, olanzapine, haloperidol, clozapine), and compound groups for each dosage (the specific dosages are listed in Table 4), with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. 1 hour after the intragastric administration, apomorphine was subcutaneously injected (1 mg/kg), with the volume as 0.1 ml/10 g. After the injection of apomorphine, the mice were immediately put into the clambering cages. After 5 min of adaptation, the behaviors of the mice at 10-11, 20-21, and 30-31 min after the injection of apomorphine were observed and scored. Scoring criteria: 4 paws on the floor was scored as 0; 2 forepaws on the cage was scored as 1; and 4 paws on the cage was scored as 2.

Example 29

Catalepsy Assay

Animals

Healthy mice of Kunming breed (with half male and half female, (22±2) g) were provided by Qinglongshan Animal Cultivation Center, Nanjing.

Main reagents: the test drugs, haloperidol, clozapine, risperidone, olanzapine, aripiprazole, ziprasidone.

Instruments: self-made bar-grabbing apparatus: stainless steel bar in mice box, which was 0.3 cm in diameter and 5 cm above the bench.

Procedures

KM mice (half male and half female, with body weight of 20-24 g) were randomly divided into negative control group, model group, positive drug groups for each dosage (risperidone, aripiprazole, ziprasidone, quetiapine, olanzapine, haloperidol, clozapine), and compound groups for each dosage, with 10 mice in each group. Corresponding solvent double-distilled water was administered intragastrically to the negative control group and the model group, corresponding positive drugs were administered intragastrically to the positive drug groups (a small amount of acetic acid was first added and then double-distilled water was added when dissolving), and corresponding dosages of compounds were administered intragastrically to the compound groups for each dosage, with the volume for intragastric administration as 0.1 ml/10 g. At 30 min, 60 min, 90 min after the intragastric administration, the two forepaws of the mice were gently placed on the bars (which were 20 cm in length, 0.3 cm in diameter, and 5.5 cm above the bench), and the hindpaws of the animals were placed on the bottom of the box. The durations for the mice to maintain the posture with the two forepaws on the bars were recorded, and 30 s of spasticity without moving was considered as the positive response. In the case the forepaws of the mice were not put down persistently, the observation was terminated at 60 s. The numbers of animals with positive response in each of the compound dosage groups were counted.

Example 30

Acute Toxicity Study

Limit Test of Sequential Assay

KM mice (half male and half female) were randomly divided into several groups (with 2-5 mice in each group), which were respectively the 2000 mg/kg groups for each compound, and the solvent group. 0.2 ml/10 g were administered intragastrically. The death of the animals in 3 days were observed. (In the case 3 or more animals survived in 3 days without notable abnormity in their life states, the observation was continued until the assay was completed in 7 days. In the case 3 or more animals died in 3 days, the median lethal dose method was used to determine the $LD_{50}$).

Pre-Assay for the Median Lethal Dose Method

KM mice (half male and half female) were randomly divided into several groups (with 4 mice in each group), which were respectively the 1500 mg/kg, 1000 mg/kg, 500 mg/kg groups for each compound, and the solvent group. 0.2 ml/10 g were administered intragastrically, and the death of the animals in 1-3 days were observed.

Results

The $LD_{50}$ of single intragastric administration of compound 7 in mice was greater than 2000 mg/kg, which was comparable to ziprasidone (>2000 mg/kg), and was far greater than risperidone (82.1 mg/kg) and aripiprazole (93 mg/kg), indicating a relatively low acute toxicity.

TABLE 2

The inhibition or $IC_{50}$ of the compounds for each receptor

| Compound No. | $D_2$ inhibition % or ($IC_{50}$, nM) | $5HT_{1A}$ inhibition % or ($IC_{50}$, nM) | $5HT_{2A}$ inhibition % or ($IC_{50}$, nM) | $D_3$ ($IC_{50}$, nM) | $5HT_{2C}$ ($IC_{50}$, nM) |
|---|---|---|---|---|---|
| 1 | 3.3% | 102.6% | 82.9% | — | — |
| 2 | 11.5% | 65.8% | 14.3% | — | — |
| 3 | 17.2% | 104.1% | 62.2% | — | — |
| 4 | 50.2% | 115.5% | 111.5% | — | — |
| 5 | $5.6^a$ | $0.03^a$ | $0.56^a$ | $8.9^a$ | $1156.3^a$ |
| 6 | 4.7% | 95.5% | 75.4% | — | — |
| 7 | $2.1^a$ | $0.08^a$ | $0.78^a$ | $7.4^a$ | $1300.6^a$ |
| 8 | 26.4% | 62.8% | 23.4% | — | — |
| 9 | 15.2% | 104.4% | 119.2% | — | — |
| 10 | 5.7% | 42.5% | 68.4% | — | — |
| 11 | 59.2% | 106.1% | 104.63% | — | — |
| 12 | 61.2% | 103.9% | 106.6% | — | — |
| 13 | 59.2% | 106.1% | 104.6% | — | — |
| 14 | $10.1^a$ | $0.86^a$ | $0.82^a$ | $15.1^a$ | $1489.2^a$ |
| 15 | $8.1^a$ | $0.73^a$ | $0.29^a$ | $8.6^a$ | $1893.6^a$ |
| 16 | 51.5% | 55.3% | 88.4% | — | — |
| 17 | 15.4% | 114.9% | 104.3% | — | — |
| 18 | 80.6% | 46.6% | 113.5% | — | — |
| 19 | $3.6^a$ | $4.2^a$ | $1.8^a$ | $13.2^a$ | $1123.3^a$ |
| 20 | 66.4% | 100.1% | 90.7% | — | — |
| 21 | 45.5% | 54.3% | 97.1% | — | — |
| aripiprazole | $24.3^a$ | $3.3^a$ | $11.5^a$ | $37.9^a$ | $25.7^a$ |

(Note: "a" indicates that the data in the cell is $IC_{50}$ value)

TABLE 3

Results of the in vivo animal model assay of the preferable compounds

| Compound No. | LD$_{50}$ (po, mg/kg) | MK-801 induced high activity (ED$_{50}$, po, mg/kg) | apomorphine induced clambering (ED$_{50}$, po, mg/kg) | catalepsy (ED$_{50}$, po, mg/kg) | catalepsy/ MK-801 induced high activity | catalepsy/ apomorphine induced clambering |
|---|---|---|---|---|---|---|
| 5 | >2000 | 0.35 | 0.68 | 168.32 | 480.91 | 247.53 |
| 7 | >2000 | 2.05 | 0.13 | 261.49 | 127.56 | 2011.46 |
| 14 | >2000 | 0.82 | 0.25 | 189.25 | 230.79 | 757 |
| 15 | >2000 | 1.25 | 0.56 | 98.86 | 79.09 | 176.54 |
| 19 | >2000 | 2.35 | 0.15 | 156.35 | 66.53 | 1042.33 |
| haloperidol | 20 | 7.42 | 0.10 | 0.44 | 4.40 | 4.89 |
| clozapine | 150 | 2.28 | 17.92 | >50 | >21.93 | >5.58 |
| risperidone | 82.1 | 0.01 | 0.015 | 0.92 | 92.00 | 61.33 |
| olanzapine | 177 | 0.10 | 0.11 | 2.23 | 22.30 | 20.27 |
| aripiprazole | 93 | 0.12 | 0.66 | 2.40 | 20.00 | 11.43 |
| ziprasidone | >2000 | 0.56 | 0.37 | 30.40 | 54.29 | 82.16 |
| quetiapine | 800 | 10.1 | 2.02 | 800.00 | 79.21 | 396.04 |

TABLE 4

Effect of the compounds on the apomorphine induced mice schizophrenia clambering model ($\bar{x} \pm s$, n = 10)

| Group | Dosage (mg/kg) | Scoring (value) |
|---|---|---|
| Negative Control Group | — | 2.69 ± 1.75 |
| Model Group | — | 5.60 ± 0.97## |
| 5 | 3 | 0.20 ± 0.63** |
|  | 1 | 0.90 ± 1.20** |
|  | 0.3 | 3.00 ± 1.94** |
|  | 0.1 | 4.60 ± 2.07 |
| 7 | 100 | 0.00 ± 0.00** |
|  | 30 | 1.80 ± 1.40** |
|  | 10 | 2.60 ± 1.58** |
|  | 3 | 3.50 ± 1.96** |
| 14 | 10 | 0.80 ± 1.40** |
|  | 3 | 0.25 ± 0.71** |
|  | 1 | 1.25 ± 1.75** |
|  | 0.3 | 2.10 ± 1.85** |
|  | 0.1 | 5.30 ± 1.25 |
| 15 | 3 | 0.50 ± 0.76** |
|  | 1 | 3.00 ± 1.60** |
|  | 0.3 | 3.38 ± 0.92** |
|  | 0.1 | 4.75 ± 1.58 |
| 19 | 3 | 0.40 ± 0.97** |
|  | 1 | 1.50 ± 1.20** |
|  | 0.3 | 4.90 ± 1.10 |
|  | 0.52 | 0.75 ± 1.04** |
| risperidone | 0.3 | 0.20 ± 0.63** |
|  | 0.1 | 1.80 ± 1.32** |
|  | 0.03 | 2.70 ± 1.77** |
|  | 0.01 | 5.20 ± 1.87 |
| aripiprazole | 10 | 0.20 ± 0.42** |
|  | 3 | 2.30 ± 1.57** |
|  | 1 | 1.5 ± 1.08** |
|  | 0.3 | 4.50 ± 1.51 |
| ziprasidone | 10 | 0.40 ± 0.84** |
|  | 3 | 0.70 ± 1.16** |
|  | 1 | 3.80 ± 1.40** |
|  | 0.3 | 4.40 ± 2.01 |
| quetiapine | 300 | 0.50 ± 1.07** |
|  | 100 | 2.60 ± 2.55** |
|  | 30 | 4.00 ± 2.31* |
|  | 10 | 3.00 ± 1.63** |
|  | 3 | 4.00 ± 2.05* |
| olanzapine | 3 | 0.30 ± 0.48** |
|  | 1 | 1.30 ± 1.25** |
|  | 0.3 | 2.10 ± 1.10** |
|  | 0.1 | 5.00 ± 1.25 |
| clozapine | 30 | 0.60 ± 1.07** |
|  | 23 | 3.70 ± 2.21* |
|  | 17.4 | 4.60 ± 2.07 |
| haloperidol | 1 | 0.60 ± 1.58** |
|  | 0.3 | 0.70 ± 0.82** |
|  | 0.23 | 0.80 ± 0.79** |
|  | 0.174 | 2.20 ± 1.69** |
|  | 0.13 | 1.50 ± 1.27** |
|  | 0.1 | 4.50 ± 1.78 |

TABLE 5

Comparison of the Animal Models

| Patent | Compound No. | LD$_{50}$ (po, mg/kg) | MK-801 induced high activity (A) (ED$_{50}$, po, mg/kg) | apomorphine induced clambering (B) (ED$_{50}$, po, mg/kg) | catalepsy (C) (ED$_{50}$, po, mg/kg) | C/A | C/B |
|---|---|---|---|---|---|---|---|
| CN 201110086701.8 | 1 | >2000 | 0.61 | 0.32 | 1.41 | 2.35 | 4.41 |
|  | 6 | >2000 | 0.32 | 0.11 | 0.68 | 2.13 | 6.18 |
|  | 7 | 1000-2000 | 0.27 | 0.15 | 1.50 | 5.56 | 10.00 |
|  | 19 | >2000 | 1.33 | 1.68 | 70.85 | 53.27 | 42.17 |
|  | 23 | >2000 | 4.24 | 0.21 | 46.14 | 10.88 | 219.71 |

TABLE 5-continued

Comparison of the Animal Models

| Patent | Compound No. | LD$_{50}$ (po, mg/kg) | MK-801 induced high activity (A) (ED$_{50}$, po, mg/kg) | apomorphine induced clambering (B) (ED$_{50}$, po, mg/kg) | catalepsy (C) (ED$_{50}$, po, mg/kg) | C/A | C/B |
|---|---|---|---|---|---|---|---|
| The present Invention | 5 | >2000 | 0.35 | 0.68 | 168.32 | 480.91 | 247.53 |
| | 7 | >2000 | 2.05 | 0.13 | 261.49 | 127.56 | 2011.46 |
| | 14 | >2000 | 0.82 | 0.25 | 189.25 | 230.79 | 757 |
| | 15 | >2000 | 1.25 | 0.56 | 98.86 | 79.09 | 176.54 |
| | 19 | >2000 | 2.35 | 0.15 | 156.35 | 66.53 | 1042.33 |
| haloperidol | | 20 | 7.42 | 0.10 | 0.44 | 4.40 | 4.89 |
| clozapine | | 150 | 2.28 | 17.92 | >50 | 21.93 | >5.58 |
| risperidone | | 82.1 | 0.01 | 0.015 | 0.92 | 92.00 | 61.33 |
| olanzapine | | 177 | 0.10 | 0.11 | 2.23 | 22.30 | 20.27 |
| aripiprazole | | 93 | 0.12 | 0.66 | 2.40 | 20.00 | 11.43 |
| ziprasidone | | >2000 | 0.56 | 0.37 | 30.40 | 54.29 | 82.16 |
| quetiapine | | 800 | 10.1 | 2.02 | 800.00 | 79.21 | 396.04 |

TABLE 6

Comparison of Results of the In Vitro Receptor Assays

| Patent | Compound No. | D2 inhibition % | 5HT$_{1A}$ (IC$_{50}$, nM) | 5HT$_{2A}$ (IC$_{50}$, nM) | D3 inhibition % | 5HT$_{2C}$ inhibition % |
|---|---|---|---|---|---|---|
| CN 201110086701.8 | 1 | 128.3% | 9.61$^a$ | 1.53$^a$ | 97.6% | 88.0% |
| | 6 | 101.3% | 3.52$^a$ | 0.39$^a$ | 100.4% | 91.4% |
| | 7 | 102.8% | 5.95$^a$ | 0.69$^a$ | 101.1% | 82.0% |
| | 12 | 124.1% | 127.3$^a$ | 9.26$^a$ | 103.1% | 93.4% |
| | 18 | 113.3% | 6.19$^a$ | 0.79$^a$ | 103.3% | 77.6% |
| | 22 | 111.8% | 12.81$^a$ | 6.88$^a$ | 103.8% | 99.8% |

| | Compound No. | D$_2$ (IC$_{50}$, nM) | 5HT$_{1A}$ (IC$_{50}$, nM) | 5HT$_{2A}$ (IC$_{50}$, nM) | D$_3$ (IC$_{50}$, nM) | 5HT$_{2C}$ (IC$_{50}$, nM) |
|---|---|---|---|---|---|---|
| The Present Invention | 5 | 5.6$^a$ | 0.03$^a$ | 0.56$^a$ | 8.9$^a$ | 1156.3$^a$ |
| | 7 | 2.1$^a$ | 0.08$^a$ | 0.78$^a$ | 7.4$^a$ | 1300.6$^a$ |
| | 14 | 10.1$^a$ | 0.86$^a$ | 0.82$^a$ | 15.1$^a$ | 1489.2$^a$ |
| | 15 | 8.1$^a$ | 0.73$^a$ | 0.29$^a$ | 8.6$^a$ | 1893.6$^a$ |
| | 19 | 3.6$^a$ | 4.2$^a$ | 1.8$^a$ | 13.2$^a$ | 1123.3$^a$ |
| aripiprazole | | 24.3$^a$ | 3.3$^a$ | 11.5$^a$ | 37.9$^a$ | 25.7$^a$ |

Example 31

Tablet

| | |
|---|---|
| Active Ingredient (the compound according to the invention) | 100 mg |
| microcrystalline cellulose | 50 mg |
| lactose | 100 mg |
| Povidone K30 | 9 mg |
| carboxymethyl starch sodium | 12 mg |
| silica | 2.5 mg |
| magnesium stearate | 1.5 mg |

The raw excipients were sieved with 80 mesh for use. The prescription doses of active ingredient, microcrystalline cellulose, lactose, Povidone K30 were weighed and introduced into a high speed mixing granulator, whereby they were mixed uniformly at low speed. A suitable amount of purified water was added, the stirring was performed at low speed, and high speed shear granulation was carried out. The wet granules were dried at 60° C. for 3 h, and sieved with 24 mesh. The prescription doses of carboxymethyl starch sodium, silica and magnesium stearate were added for mixing totally. The compression was performed in a rotary tablet press.

Example 32

Capsule

| | |
|---|---|
| Active Ingredient (the compound according to the invention) | 100 mg |
| lactose | 80 mg |
| starch | 40 mg |
| Povidone K30 | 7 mg |
| silica | 2 mg |
| magnesium stearate | 1 mg |

The raw excipients were sieved with 80 mesh for use. The prescription doses of active ingredient, lactose, starch, Povidone K30 were weighed and introduced into a high speed mixing granulator, whereby they were mixed uniformly at low speed. A suitable amount of purified water was added, the stirring was performed at low speed, and high speed shear granulation was carried out. The wet granules were dried at 60° C. for 3 h, and sieved with 24 mesh. The prescription doses of silica and magnesium stearate were added for mixing totally. The capsules were filled in a capsule filling machine.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

What is claimed is:

1. A compound of formula I or a salt thereof:

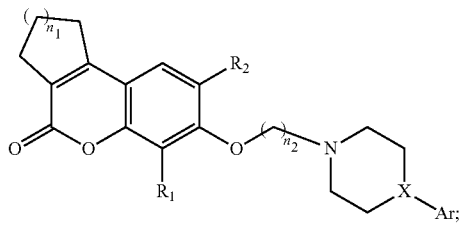

I

Wherein:
$n_1$ is 1, 2 or 3;
$n_2$ is 3, 4 or 5;
X is CH or N;
Ar has formula II or formula III:

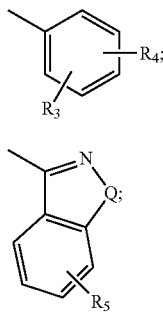

II

III

Wherein:
Q is O or S; and
$R_1$, $R_2$, $R_3$, $R_4$ and $R_5$ are each independently H, halogen, unsubstituted $C_1$-$C_5$ alkyl, $C_1$-$C_5$ alkyl substituted by halogen, unsubstituted $C_1$-$C_5$ alkoxy, or $C_1$-$C_5$ alkoxy substituted by halogen.

2. The compound according to claim 1 or the salt thereof, wherein the halogen substitution in $C_1$-$C_5$ alkyl is F.

3. The compound according to claim 2 or the salt thereof, wherein the F substituted $C_1$-$C_5$ alkyl is trifluoromethyl.

4. The compound according to claim 1 or the salt thereof, wherein the unsubstituted $C_1$-$C_5$ alkyl is $C_1$ and $C_1$ is methyl.

5. The compound according to claim 2 or the salt thereof, wherein the F substituted $C_1$-$C_5$ alkyl is $C_1$ and $C_1$ is methyl.

6. The compound according to claim 1 or the salt thereof, wherein the unsubstituted $C_1$-$C_5$ alkoxy is $c_1$ and $C_1$ is methoxy.

7. The compound according to claim 1 or the salt thereof, wherein at least one $R_1$, $R_2$, $R_3$, $R_4$ or $R_5$ is halogen and the halogen is Cl or F.

8. The compound according to claim 1 or the salt thereof, wherein $n_1$ is 1 or 2 and $n_2$ is 3 or 4, and $R_1$ or $R_2$ is selected from the group consisting of H, halogen, and $C_1$-$C_5$ alkyl.

9. The compound according to claim 8 or the salt thereof, wherein $R_1$ or $R_2$ is selected from the group consisting of H, Cl, and methyl.

10. The compound according to claim 1 or the salt thereof, wherein when Ar has the formula II, then:
X is N; and
$R_3$ or $R_4$ is selected from the group consisting of H, halogen, $C_1$-$C_5$ alkyl, $C_1$-$C_5$ alkyl substituted by halogen, $C_1$-$C_5$ alkoxy, and $C_1$-$C_5$ alkoxy substituted by halogen.

11. The compound according to claim 10 or the salt thereof, wherein $R_3$ or $R_4$ is selected from the group consisting of Cl, F, methyl, trifluoromethyl, and methoxy.

12. The compound according to claim 1 or the salt thereof, wherein when Ar has the formula III, then:
Q is O or S;
X is selected from the group consisting of N and CH; and
$R_5$ is H or halogen.

13. The compound according to claim 12 or the salt thereof, wherein $R_5$ is F.

14. The compound according to claim 1 or the salt thereof, which is the following compound or the salt thereof:
(1) 7-{3-[4-(2,3-dimethylphenyl)piperazin-1-yl]-propoxy}-2,3-dihydro-1H-cyclopenteno[c]benzopyran-4-one;
(2) 7-{3-[4-(2,3-dichlorophenyl)piperazin-1-yl]-propoxy}-2,3-dihydro-1H-cyclopenteno[c]benzopyran-4-one;
(3) 7-{3-[4-(3-trifluoromethylphenyl)piperazin-1-yl]-propoxy}-2,3-dihydro-1H-cyclopenteno[c]benzopyran-4-one;
(4) 7-{3-[4-(2-methoxyphenyl)piperazin-1-yl]-propoxy}-2,3-dihydro-1H-cyclopenteno[c]benzopyran-4-one;
(5) 7-{3-[4-(3-(6-fluoro-benzisoxazole)-1-piperidyl)-n-propoxy]}-2,3-dihydro-1H-cyclopenteno[c]benzopyran-4-one;
(6) 7-{3-[4-(2-methoxyphenyl)piperazin-1-yl]-propoxy}-6-methyl-2,3-dihydro-1H-cyclopenteno[c]benzopyran-4-one;
(7) 7-{4-[4-(2-methoxyphenyl)piperazin-1-yl]-butoxy}-2,3-dihydro-1H-cyclopenteno[c]benzopyran-4-one;
(8) 7-{4-[4-(4-methoxyphenyl)piperazin-1-yl]-butoxy}-2,3-dihydro-1H-cyclopenteno[c]benzopyran-4-one;
(9) 7-{4-[4-(4-fluorophenyl)piperazin-1-yl]-butoxy}-2,3-dihydro-1H-cyclopenteno[c]benzopyran-4-one;
(10) 7-{4-[4-(3-(6-fluoro-benzisoxazole)-1-piperidyl)-butoxy]}-2,3-dihydro-1H-cyclopenteno[c]benzopyran-4-one;
(11) 7-{4-[4-(2-methoxyphenyl)piperazin-1-yl]-butoxy}-6-methyl-2,3-dihydro-1H-cyclopenteno[c]benzopyran-4-one;
(12) 7-{4-[4-(3-(1,2-benzisothiazole)-1-piperazinyl)-butoxy]}-6-methyl-2,3-dihydro-1H-cyclopenteno[c]benzopyran-4-one;
(13) 7-{4-[4-(2-methoxyphenyl)piperazin-1-yl]-butoxy}-6-chloro-2,3-dihydro-1H-cyclopenteno[c]benzopyran-4-one;

(14) 7-{4-[4-(3-(1,2-benzisothiazole)-1-piperazinyl)-n-butoxy]}-6-chloro-2,3-dihydro-1H-cyclopenteno[c]benzopyran-4-one;

(15) 7-{4-[4-(3-(6-fluoro-benzisoxazole)-1-piperidyl)-butoxy]}-6-chloro-2,3-dihydro-1H-cyclopenteno[c]benzopyran-4-one;

(16) 7-{4-[4-(3-(6-fluoro-benzisoxazole)-1-piperidyl)-butoxy]}-8-chloro-2,3-dihydro-1H-cyclopenteno[c]benzopyran-4-one;

(17) 7-{4-[4-(2-methoxyphenyl)piperazin-1-yl-butoxy]}-8-chloro-2,3-dihydro-1H-cyclopenteno[c]benzopyran-4-one;

(18) 3-{4-[4-(3-(6-fluoro-benzisoxazole)-1-piperidyl)-butoxy]}-7,8,9,10-tetrahydrobenzo[c]benzopyran-6-one;

(19) 3-{4-[4-(2-methoxyphenyl)piperazin-1-yl]-butoxy}-7,8,9,10-tetrahydrobenzo[c]benzopyran-6-one;

(20) 3-{4-[4-(2-methoxyphenyl)piperazin-1-yl]-butoxy}-4-methyl-7,8,9,10-tetrahydrobenzo[c]benzopyran-6-one; or

(21) 3-{4-[4-(3-(6-fluoro-benzisoxazole)-1-piperidyl)-butoxy]}-4-methyl-7,8,9,10-tetrahydrobenzo[c]benzopyran-6-one.

15. The salt of the compound according to claim 1, wherein the salt contains a pharmaceutically acceptable anion.

16. A pharmaceutical composition comprising:
the compound according to claim 1 or the salt thereof in a therapeutically effective amount; and
a pharmaceutically acceptable carrier.

17. A method for treating schizophrenia, comprising:
administrating the compound according to claim 1 or the salt thereof to a patient in need thereof.

* * * * *